United States Patent
Rouw et al.

(10) Patent No.: US 6,748,270 B2
(45) Date of Patent: Jun. 8, 2004

(54) METHOD AND SYSTEM FOR NODAL RHYTHM DETECTION AND TREATMENT

(75) Inventors: Mattias Rouw, Arnhem (NL); Gustaaf A. P. Stoop, Dieren (NL)

(73) Assignee: Medtronic Inc., Minneapolis, MN (US)

( * ) Notice: Subject to any disclaimer, the term of this patent is extended or adjusted under 35 U.S.C. 154(b) by 305 days.

(21) Appl. No.: 09/842,812

(22) Filed: Apr. 27, 2001

(65) Prior Publication Data

US 2002/0161409 A1 Oct. 31, 2002

(51) Int. Cl.[7] ............................................. A61N 1/362
(52) U.S. Cl. ...................................................... 607/9
(58) Field of Search ............................. 607/9, 14, 25; 600/515, 516, 518

(56) References Cited

U.S. PATENT DOCUMENTS

| | | | |
|---|---|---|---|
| 4,284,082 A | * | 8/1981 | Funke et al. ................... 607/9 |
| 4,316,472 A | | 2/1982 | Mirowski et al. |
| 4,375,817 A | | 3/1983 | Engle et al. |
| 4,379,459 A | | 4/1983 | Stein |
| 4,384,585 A | | 5/1983 | Zipes |
| 4,556,063 A | | 12/1985 | Thompson et al. |
| 4,577,633 A | | 3/1986 | Berkovits et al. |
| 4,587,970 A | | 5/1986 | Holley et al. |
| 4,726,380 A | | 2/1988 | Vollmann et al. |
| 4,727,877 A | | 3/1988 | Kallok |
| 4,821,723 A | | 4/1989 | Baker et al. |
| 4,830,006 A | | 5/1989 | Haluska et al. |
| 4,880,005 A | | 11/1989 | Pless |
| 4,949,719 A | | 8/1990 | Pless |
| 5,131,388 A | | 7/1992 | Pless |
| 5,188,105 A | | 2/1993 | Keimel et al. |
| 5,199,428 A | | 4/1993 | Obel et al. |
| 5,207,218 A | | 5/1993 | Carpentier et al. |
| 5,312,453 A | | 5/1994 | Shelton et al. |
| 5,314,430 A | | 5/1994 | Bardy |
| 5,330,507 A | | 7/1994 | Schwartz |
| 5,331,966 A | | 7/1994 | Bennett et al. |
| 5,354,316 A | | 10/1994 | Keimel et al. |
| 5,379,776 A | * | 1/1995 | Murphy et al. ............. 600/518 |
| 5,545,186 A | | 8/1996 | Olson |
| 6,493,583 B1 | * | 12/2002 | Levine et al. .................. 607/9 |

OTHER PUBLICATIONS

"Automatic Tachycardia Recognition" Arzbaecher et al. PACE, May–Jun. 1984 p. 541–547.

* cited by examiner

Primary Examiner—Kennedy Schaetzle
(74) Attorney, Agent, or Firm—Girma Wolde-Michael

(57) ABSTRACT

A method and system for nodal rhythm detection and treatment is provided. Detecting consecutive atrial events within a nodal activity window around ventricular events identifies nodal rhythm. Nodal rhythm is treated by calculating and applying a new atrial escape interval adjusted by the interval between the atrial and ventricular events.

23 Claims, 9 Drawing Sheets

METHOD AND SYSTEM FOR NODAL RHYTHM DETECTION AND TREATMENT

FIELD OF THE INVENTION

The present invention relates to the field of implantable medical devices, more particularly, to cardiac pacing systems having nodal rhythm detection and treatment.

BACKGROUND OF THE INVENTION

Implantable cardiac pacing systems deliver a pacing signal to stimulate a heart chamber. The pacing signal is typically delivered by an electrode in the heart chamber. The same electrode is also used to sense electrical activity indicating an intrinsic contraction of the heart chamber. The presence or absence of the sensed activity and the timing of the sensed contractions, are used to control the cardiac pacing system for the patient's well being.

In AV nodal rhythm, the intrinsic AV pacemaker controls the ventricles and atria. The nodal rhythm can result from anything that suppresses sinus node activity, such as sinus bradycardia; any form of vagal stimulation; digitalis; the initial phase of atropine action; SA block; or congenital absence of the SA node. The AV nodal rate will usually be less than 50 beats per minute.

AV nodal rhythm may also occur from anything that enhances AV nodal rhythm, such as digitalis intoxication, rheumatic fever, or inferior myocardial infarction. The AV nodal rate will usually be between 60 and 100 beats per minute. This is also called accelerated AV (nodal) rhythm.

Sherlag et al. present evidence of that there are at least two varieties of AV junctional rhythm: true AV nodal rhythm of 30 to 40 bpm increased under influence of atropine, and His bundle rhythm of 20 to 25 bpm little affected by atropine. Scherlag, B. J., Lazzara, R. Helfant, R. H., *Differentiation of A-V Junctional Rhythms*, Circulation, 48:304, 1973.

Currently AV nodal rhythm can be treated with medication, or by cardiac stimulation. Medication may be ineffective or have undesirable effects. Surgical intervention can be used to remove or reduce the AV conduction system, but runs the risks inherent in any surgical procedure, as well as uncertainty as to result.

During AV nodal rhythm, atrial contraction takes place during ventricular contraction. The blood in the atria is forced back into the venous system and may cause clinical symptoms such as venous pulsations in the jugular area and in the abdomen. Through an increased venous pressure because of the regurgitation into the venous system, inappropriate baroreceptor reflexes may cause acute drops in blood pressure.

The most pertinent prior art references known at the present time are the following:

In "Transesophageal Atrial Pacing For Intraoperative Sinus Bradycardia Or AV Junctional Rhythm: Feasibility As Prophylaxis In 200 Anesthetized Adults And Hemodynamic Effects Of Treatment," Atlee et al., J Cardiothorac Vasc Anesth 1993 Aug;7(4):436–41, Atlee et al. reported that transesophageal atrial pacing (TAP) at a rate sufficient to overdrive atrioventricular junctional rhythm (AVJR) was effective initial treatment in all patients tested. Feasibility of TAP as prophylaxis for sinus bradycardia (SB) or AVJR was tested with approved or investigational devices in 200 anesthetized surgical patients, not necessarily with cardiovascular disease or having cardiac surgery. Thirteen patients had AVJR (72+/−4 beats/min; mean +/−SEM).

In "The Effects Of Overdrive Pacing And Lidocaine On Atrioventricular Junctional Rhythm In Man: The Role Of Abnormal Automaticity," Tenczer et al., Circulation 1985 Sep;72(3):480–6, Tenczer et al. reported AV junctional rhythms in group I (17 patients) were suppressed by overdrive pacing, and their rates were decreased by lidocaine. AV junctional rhythms in group II (five patients) were not suppressed by overdrive pacing. The data suggest that AV junctional rhythms in group I were caused by normal automaticity, while those in group II were probably due to abnormal automaticity.

All prior art references above are hereby incorporated by reference herein in their respective entireties. As those of ordinary skill in the art will appreciate readily upon reading the Summary of the Invention, the Detailed Description of the Preferred Embodiments and the claims set forth below, many of the devices and methods disclosed in the prior art references may be modified advantageously by using the teachings of the present invention.

SUMMARY OF THE INVENTION

The present invention is therefore directed to providing a system and method for nodal rhythm detection and treatment. The system of the present invention overcomes the problems, disadvantages and limitations of the prior art described above, and provides a more efficient and accurate means of nodal rhythm detection and treatment.

The present invention has certain objects. That is, various embodiments of the present invention provide solutions to one or more problems existing in the prior art of nodal rhythm detection and treatment. Those problems include, without limitation: (a) need for automatic nodal rhythm detection, (b) need for automatic nodal rhythm treatment, (c) interference with intrinsic heart rhythm, (d) patient discomfort from pacemaker syndrome, and (e) patient discomfort from abrupt changes after treatment.

In comparison to known techniques for nodal rhythm detection and treatment, various embodiments of the present invention provide one or more of the following advantages: (a) the ability to automatically detect nodal rhythm, (b) the ability to automatically treat nodal rhythm using atrial pacing tuned by the AV delay, and (c) the ability to restore the intrinsic heart rhythm with an optimized hemodynamic AV delay.

Some of the embodiments of the present invention include one or more of the following features: (a) an IMD having automatic nodal rhythm detection, (b) an IMD having automatic nodal rhythm treatment that use atrial pacing tuned by the AV delay, (c) methods of performing nodal rhythm detection that use a nodal activity window, (d) methods of performing automatic nodal rhythm treatment that use atrial pacing tuned by the AV delay, and (e) methods of avoiding patient discomfort from AV nodal rhythm.

At least some embodiments of the present invention involve detecting nodal activity by looking for atrial activity in a nodal activity window around ventricular activity. If a predetermined number of successive atrial events fall within the nodal activity window, nodal rhythm is present. The nodal activity window is typically 60 ms before and 100 ms after a ventricular sense, but may be shorter and can be tuned for a specific patient. The nodal activity detection method first determines if the atrial event precedes the ventricular event (positive AV delay) or vice versa (VA delay), then looks for atrial activity between a first time limit and the ventricular activity if the atrial event precedes the ventricular event (positive AV delay), and for atrial activity between a second time limit and the ventricular activity if the ventricular event precedes the atrial event (positive VA delay). The nodal activity detection method can also calculate an appropriate initial atrial escape interval for nodal treatment if pacing is to be applied. If atrial activity occurs outside the nodal activity window before the predetermined number of successive atrial events is reached, the nodal rhythm detection counter is reset and the nodal activity detection method starts over.

Other embodiments of the present invention involve detecting nodal activity, then treating the nodal activity using pacing. The nodal rhythm detection and treatment method starts by checking for tachycardia and average ventricular rate greater than 100 beats per minute, then terminates the nodal treatment if either is found because nodal rhythm could not be occurring with those conditions. If neither condition is present, the nodal rhythm detection and treatment method checks to see if nodal treatment is active, then looks for nodal rhythm using a nodal activity detection method if it is not.

If nodal treatment is active, the nodal treatment follows different procedures depending on whether the activity is an atrial sense, an atrial pace followed by a ventricular sense, or an atrial pace followed by a ventricular pace.

An atrial sense may indicate that the nodal rhythm is in control and further adjustment of the atrial escape interval is required. The nodal treatment method looks for atrial activity in a nodal activity window around ventricular activity. The nodal activity window is typically 60 ms before and 100 ms after a ventricular sense, but may be shorter and can be tuned for a specific patient. Depending on the timing of the ventricular sense with respect to the atrial sense, the nodal treatment method calculates a new atrial escape interval to tune the atrial escape interval.

An atrial pace followed by a ventricular sense indicates that the therapy is effective. The next AV delay is further tuned based on the last ventricular sense. An atrial pace followed by a ventricular pace indicates the nodal rhythm has stopped. The pacing enters a flywheel mode in which the pacing interval is gradually increased to ease out of nodal treatment. If a predetermined number of successive atrial pace-ventricular pace sequences occur, nodal rhythm is no longer present and the nodal treatment is deactivated.

BRIEF DESCRIPTION OF THE DRAWINGS

The above, and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

Figure 1:
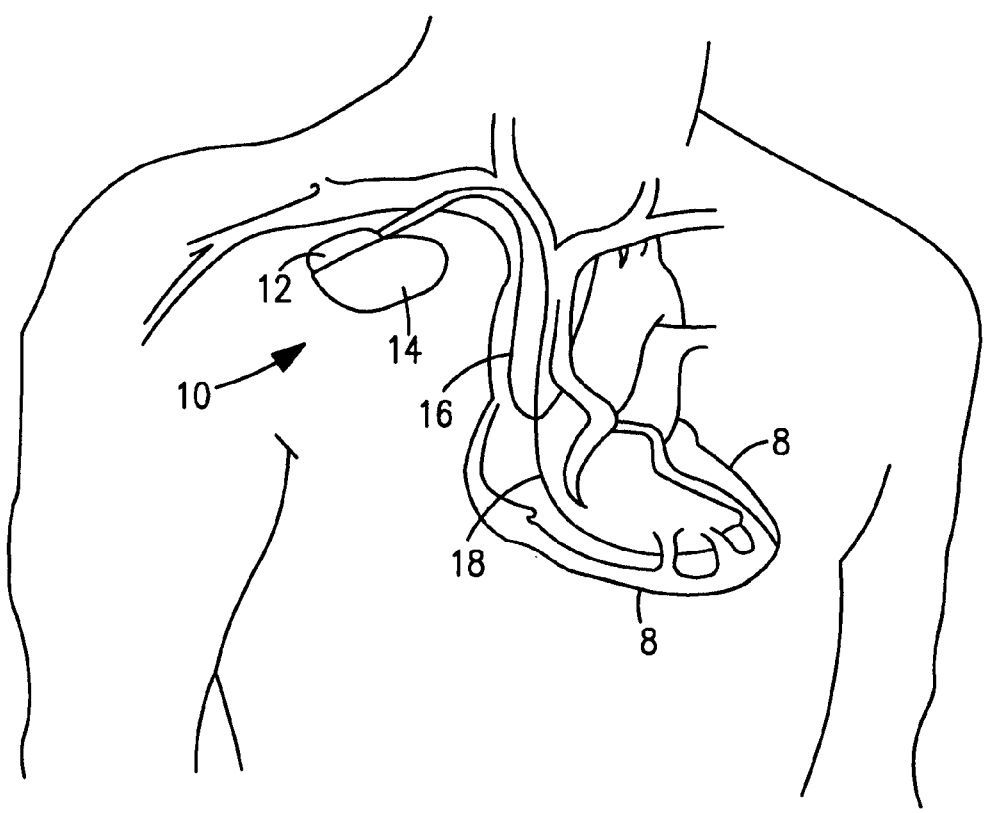
FIG. 1 is a schematic view of one embodiment of an implantable medical device in situ, made in accordance with the present invention.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and repolarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
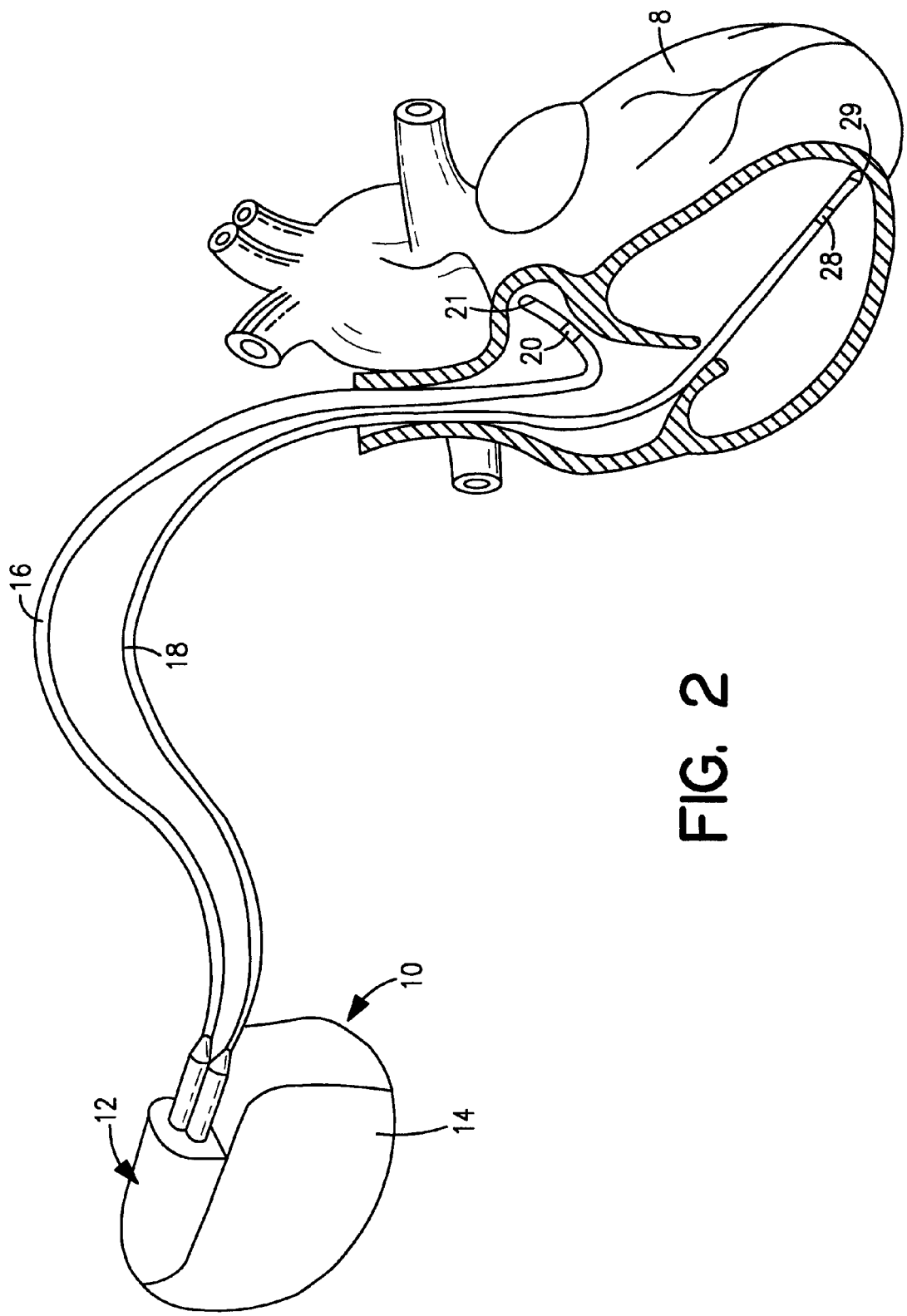
FIG. 2 is another schematic view of an embodiment of the implantable medical device of FIG. 1, made in accordance with the present invention.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
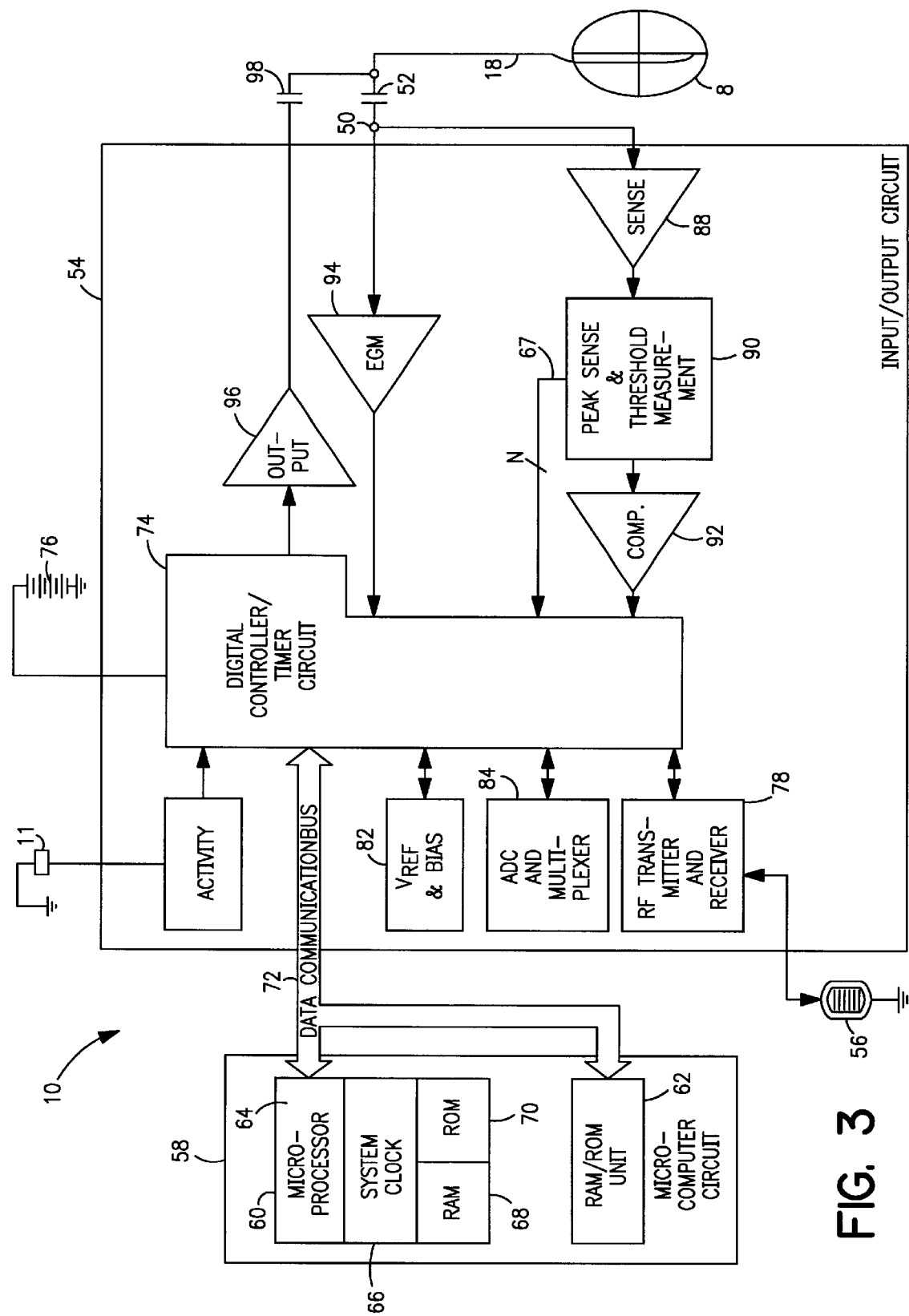
FIG. 3 is a block diagram illustrating components of an embodiment of the implantable medical device of FIG. 1, made in accordance with the present invention.

FIG. 3 shows a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. patents referenced therein.

IMD 10 may also be a pacemaker-cardioverter-defibrillator ("PCD") corresponding to any of numerous commercially available implantable PCDs. Various embodiments of the present invention may be practiced in conjunction with PCDs such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all hereby incorporated by reference herein, each in its respective entirety.

Figure 4:
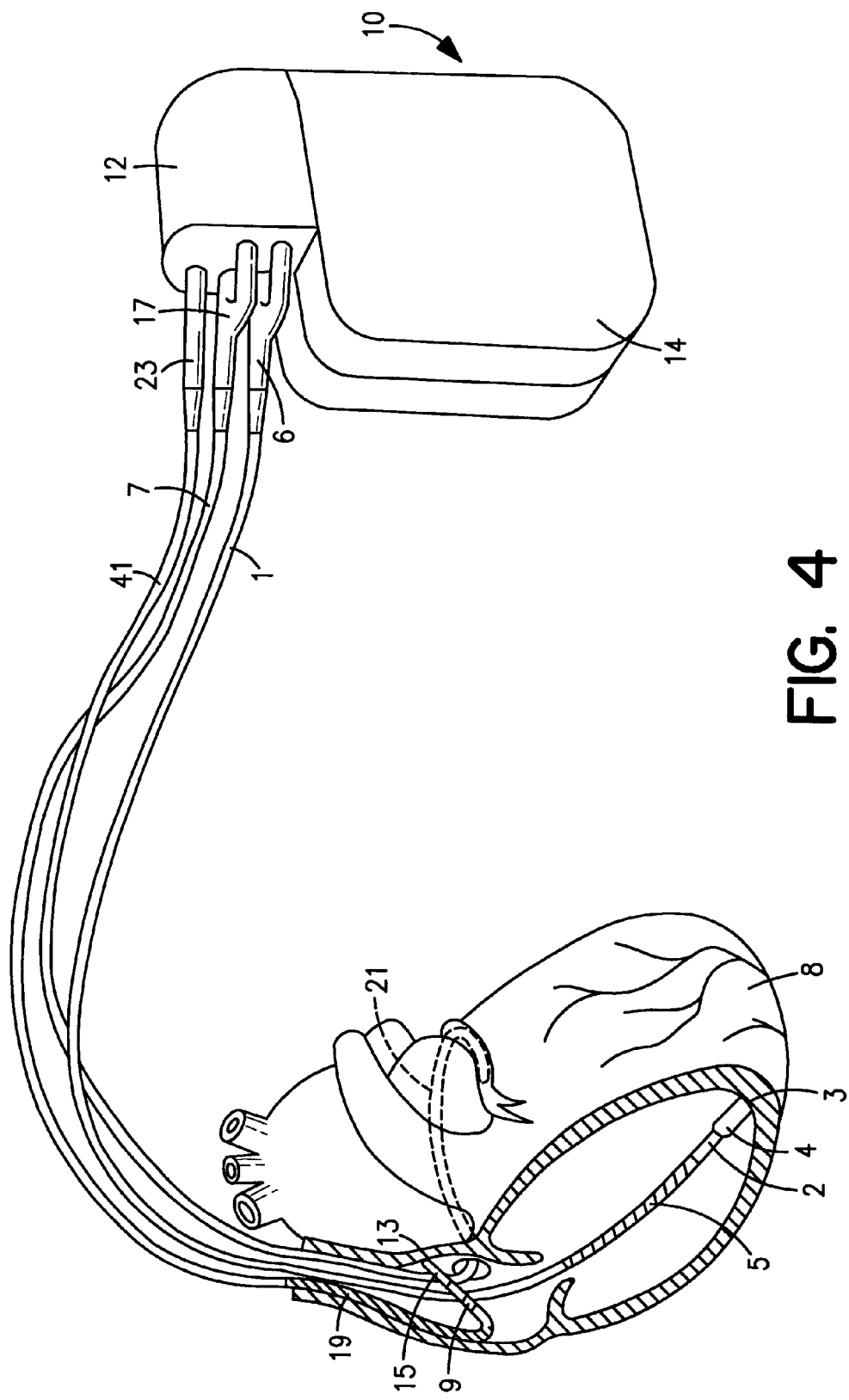
FIG. 4 is a schematic view of another embodiment of an implantable medical device, made in accordance with the present invention.
Figure 5:
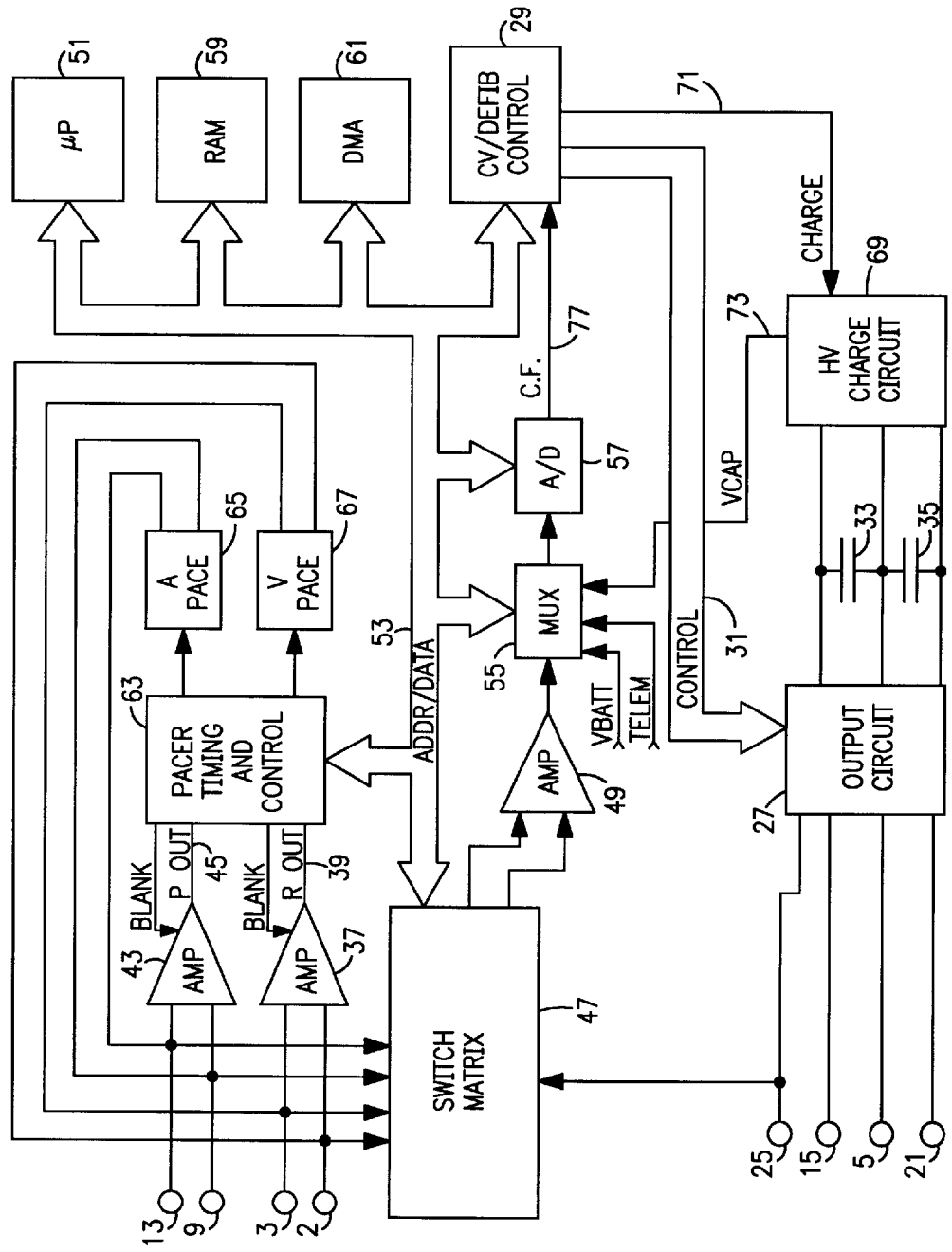
FIG. 5 is a block diagram illustrating components of an embodiment of the implantable medical device of FIG. 4, made in accordance with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6, which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 21 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10,1986, IEEE Computer Society Press, pages 167–170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May-June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23,1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to a cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches, which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Figure 6:
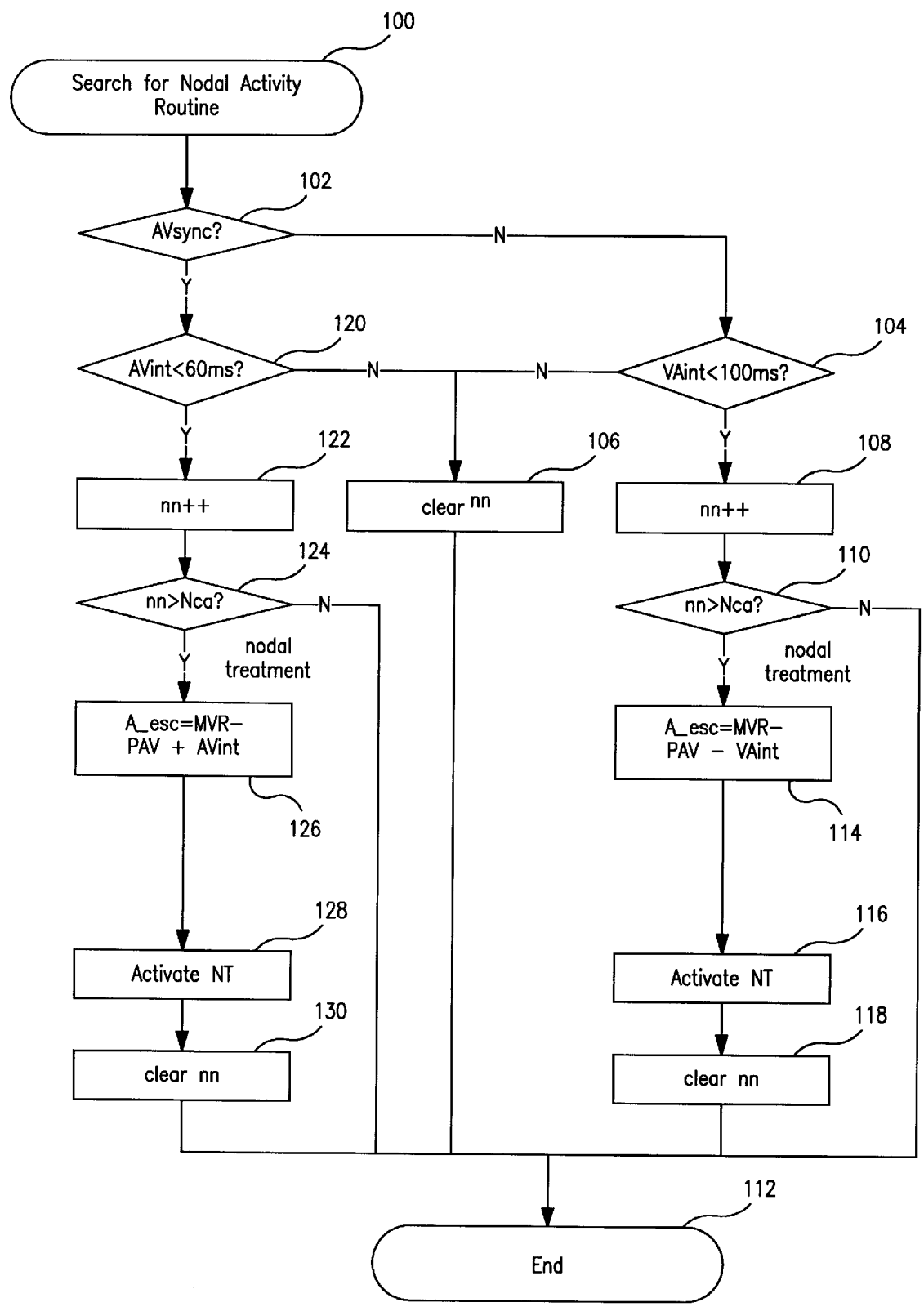
FIG. 6 is a flow chart of a method for nodal rhythm detection, in accordance with the present invention.

FIG. 6 shows a flow chart of a method for nodal rhythm detection in accordance with the present invention. An IMD 10 disposed within mammalian heart 8 is programmed to detect nodal rhythm by determining if a predetermined number of successive atrial events fall within the time period between a first time limit before a ventricular event (if the atrial event precedes the ventricular event in positive AV delay) and a second time limit after a ventricular event (if the ventricular event precedes the atrial event in positive VA delay). When this predetermined number of successive events is found, it could be a nodal rhythm. The first time limit is typically 60 ms before a ventricular event and the second time limit is typically 100 ms after a ventricular event, but the time limits vary from patient to patient and can be tuned to fit a particular patient's needs. Although the nodal rhythm detection method is presented as a method used in an IMD such as a DDD device sensing cardiac activity through the leads, in alternate embodiments the method can be used in external devices with epicardial sensors having a direct interface with the heart. In other alternate embodiments, the nodal rhythm detection method could be used to monitor a patient under observation. The nodal rhythm detection method starts at block 100 of FIG. 6. Block 102 checks whether the atrial event preceded the ventricular event. If the ventricular event preceded the atrial event, the answer is no and the method proceeds to block 104. Block 104 checks if the V-A interval, the interval between the ventricular event and atrial event, is within the second time limit and may indicate a potential nodal rhythm. If the V-A interval (VAint) is not within the second time limit (here, 100 ms) indicating that there is no nodal rhythm present, the method proceeds to block 106, which clears the nodal rhythm detection counter (nn) and the nodal rhythm detection method ends at block 112.

If the V-A interval (VAint) is within the second time limit (here, 100 ms) indicating that there may be nodal rhythm present, the method proceeds to block 108, which increments the nodal rhythm detection counter (nn). The nodal rhythm detection counter is checked against the nodal treatment activation constant (Nca) at block 110 and the nodal rhythm detection method ends at block 112 if the nodal rhythm detection counter is less than the Nca. The Nca is selected depending on the particular patient, but can be between 1 and 10, and is typically 3.

If the nodal rhythm detection counter is greater than the Nca, nodal rhythm treatment is activated. The method calculates a new atrial escape interval (A_esc) in block 114 such that the next atrial pace is delivered at a preferred AV delay before the expected ventricular sense. This is calculated as the mean ventricular rate, less the paced AV interval less the VA interval [A_esc=MVR−PAV−VAint]. The variables can be selected from the average over the successive nodal rhythm events or can be from the last set of data on reaching the Nca. The delivered PAV ranges from 90–250 ms is rate dependent and has a typical value of 150 ms. If nodal rhythm treatment is initiated, the reduced atrial escape interval will be set to a rate to terminate the nodal rhythm. A flag is set at block 116 to activate nodal rhythm treatment, the nodal rhythm detection counter (nn) is cleared at block 118, and the nodal rhythm detection method ends at block 112.

The logic is similar if the atrial event precedes the ventricular event (positive AV delay) at block 102. If the atrial event preceded the ventricular event, the method proceeds to block 120. Block 120 checks if the AV interval, the interval between the atrial event and ventricular event, is within the first time limit and may indicate a potential nodal rhythm. If the AV interval (AVint) is not within the second time limit (here, 60 ms) indicating that there is no nodal rhythm present, the method proceeds to block 106, which clears the nodal rhythm detection counter (nn) and the nodal rhythm detection method ends at block 112.

If the AV interval (AVint) is within the second time limit (here, 60 ms) indicating that there may be nodal rhythm present, the method proceeds to block 122, which increments the nodal rhythm detection counter (nn). The nodal rhythm detection counter is checked against the Nca at block 124 and the nodal rhythm detection method ends at block 112 if the nodal rhythm detection counter is less than the Nca. The Nca is selected depending on the particular patient, but can be between 1 and 10, and is typically 3.

If the nodal rhythm detection counter is greater than the Nca, nodal rhythm treatment should be activated. The method calculates a new atrial escape interval (A_esc) in block 126 as the mean ventricular rate, less the paced AV interval, plus the VA interval [A_esc=MVR−PAV+AVint]. The variables can be selected from the average over the successive nodal rhythm events or can be from the last set of data on reaching the Nca. The delivered PAV ranges from 90–250 ms is rate dependent and has a typical value of 150 ms. If nodal rhythm treatment is initiated, the reduced atrial escape interval will be set to a rate to terminate the nodal rhythm. A flag is set at block 128 to activate nodal rhythm treatment, the nodal rhythm detection counter (nn) is cleared at block 130, and the nodal rhythm detection method ends at block 112. The nodal rhythm detection method as described can be used in the nodal treatment method described in FIG. 7.

Figure 7:
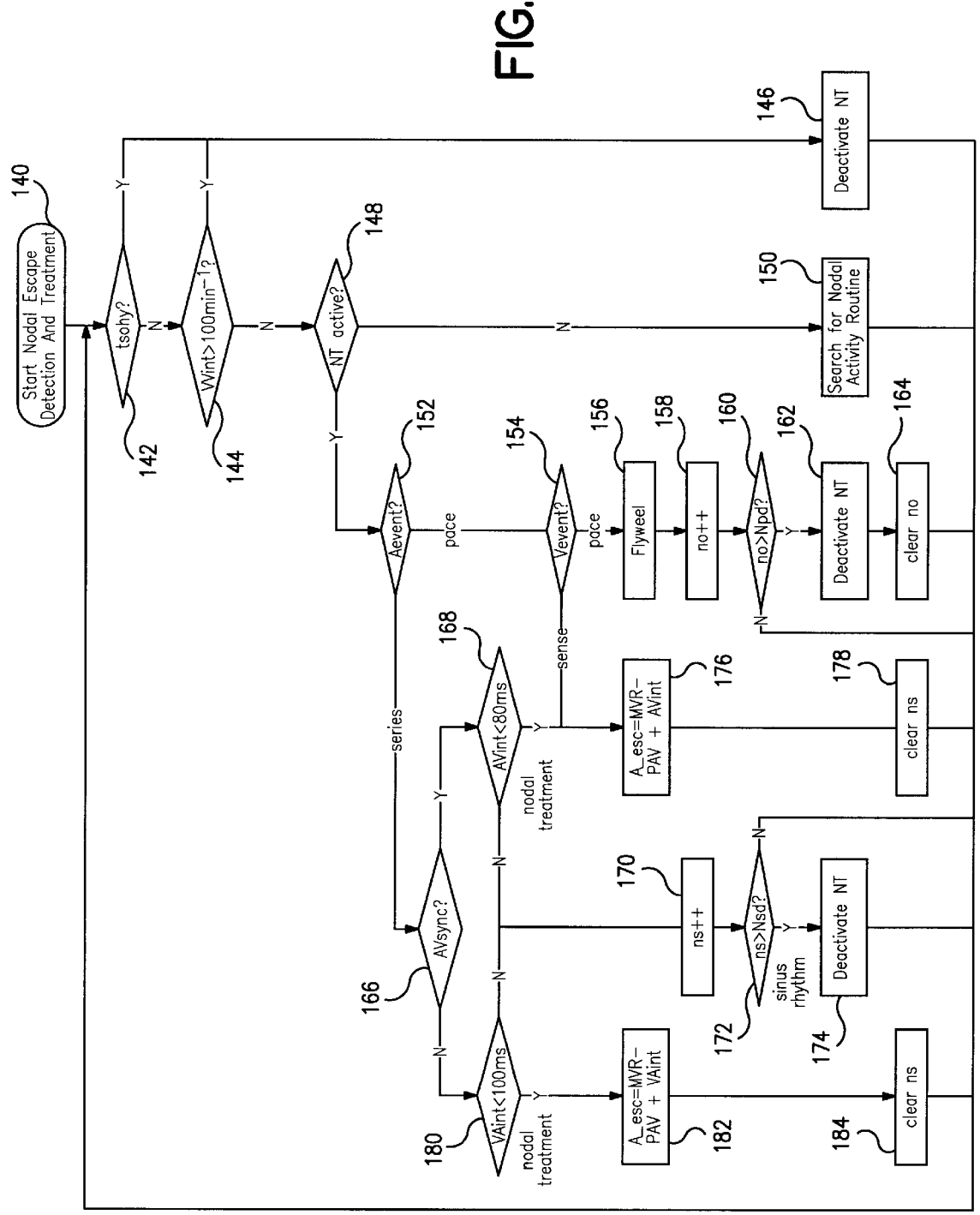
FIG. 7 is a flow chart of a method for nodal rhythm detection and treatment, in accordance with the present invention.

FIG. 7 shows a flow chart of a method for nodal rhythm detection and treatment in accordance with the present invention. An IMD 10 disposed within mammalian heart 8 is programmed to treat nodal rhythm by pacing, that is, tuning the atrial escape interval such that an optimal hemodynamic AV delay is obtained while the mean ventricular rate maintains the same. The atrial pacing is further tuned by the AV delay: if the AV delay becomes shorter, the nodal rhythm rate may overtake the atrial rate, so the atrial rate is increased. The AV delay tuning of the atrial pacing avoids pacemaker syndrome caused by nodal activity, rather than artificial pacemaker activity. The nodal treatment method allows restoration of the intrinsic rhythm with an optimized hemodynamic AV delay while maintaining ventricular intrinsic activity (either or not caused by atrial pacing or nodal rhythm).

The nodal rhythm detection and treatment method starts at block 140 of FIG. 7. If atrial tachycardia is present at block 142 (tachy?) or the average ventricular rate is greater than 100 beats per minute at block 144 (VVint>100 min$^{-1}$?), the nodal therapy is deactivated at block 146. Nodal rhythm will not occur with atrial tachycardia or high intrinsic ventricular rate, so nodal therapy is not required. If no atrial tachycardia or high intrinsic ventricular rate is present, the method proceeds to block 148 to check whether nodal therapy is active. If nodal therapy is not active, the nodal rhythm detection routine at block 150 checks for nodal rhythm. The nodal rhythm detection routine can be the nodal rhythm detection described in FIG. 6 above. When nodal rhythm is detected, the nodal rhythm detection routine is activated.

If nodal therapy is active, the method enters the nodal treatment portion of the nodal rhythm detection and treatment method at block 152. The nodal treatment portion maintains the mean ventricular rate (VVrate), and tries to restore the physiologic AVdelay. This is accomplished by delivering atrial paces at a physiologic AVdelay before the expected Vsense. Block 152 determines if the atrial event is an atrial pace or an atrial sense.

If the atrial event is an atrial pace, the method proceeds to block 154, which determines if the ventricular event is a ventricular pace or a ventricular sense. If the ventricular event is a ventricular sense, the pacing is not yet in control and further nodal treatment is required. The method proceeds to block 176 where a new atrial escape interval (A_esc) is calculated, and the sinus rhythm counter (ns) is cleared at block 178.

If in block 154 the ventricular event is a ventricular pace, the nodal rhythm might have stopped. A flywheel mode is initiated at block 156. The flywheel mode allows the pacing interval to gradually ease out of nodal treatment, rather than making an abrupt change that might cause patient concern or discomfort. The atrial escape is adjusted so the next atrial pace will be delivered at a longer interval. The method then proceeds to block 158 where the nodal counter (no) is incremented.

Block 160 checks to see if the nodal counter is greater than the predetermined nodal treatment pace deactivation constant (Npd). The Npd is selected depending on the particular patient, but can be between 1 and 10, and is typically 3. If the nodal counter is not greater than the Npd, the method returns to the start at block 140. If the nodal counter is greater than the Npd, nodal treatment is no longer required, so nodal treatment is deactivated at block 162 and the nodal counter (no) is cleared at block 164.

If block 152 determines if the atrial event is an atrial sense, the method proceeds to block 166, which starts the portion of the procedure that determines whether the atrial sense originated from the atrium or the AV node. The logic is similar to the nodal rhythm detection method presented in FIG. 6, determining if an atrial event falls within the time period between a first time limit before a ventricular event and a second time limit after a ventricular event. An atrial sense within the window may indicate that the nodal rhythm is in control and further adjustment of the atrial escape interval is required.

Block 166 checks whether the atrial event preceded the ventricular event. If the ventricular event preceded the atrial event, the answer is no and the method proceeds to block 180. Block 180 checks if the V-A interval, the interval between the ventricular event and atrial event, is within the second time limit and may indicate a potential nodal rhythm. If the V-A interval (VAint) is not within the second time limit (here, 100 ms) indicating that there is no nodal rhythm present, the method proceeds to block 170, which increments the sinus rhythm counter (ns).

Block 172 checks to see if the sinus rhythm counter is greater than the predetermined nodal treatment sinus deactivation constant (Nsd). The Nsd is selected depending on the particular patient, but can be between 1 and 10, and is typically 3. If the sinus rhythm counter is not greater than Nsd, the method returns to the start at block 140. If the sinus rhythm counter is greater than Nsd, sinus rhythm has been established and nodal treatment is no longer required, so nodal treatment is deactivated at block 174.

If the V-A interval (VAint) is within the second time limit (here, 100 ms) indicating that there may be nodal rhythm present, the method proceeds to block 182, which calculates a new escape interval. The method calculates a new atrial escape interval (A_esc) as the mean ventricular rate, less the paced AV interval less the V-A interval [A_esc =MVR−PAV−VAint]. The sinus rhythm counter (ns) is cleared at block 184.

The logic is similar at block 166 if the atrial event precedes the ventricular event (positive AV delay), only the method looks for atrial events within the first time limit of the ventricular event. If the atrial event preceded the ventricular event, the method proceeds to block 168. Block 168 checks if the A-V interval, the interval between the atrial event and ventricular event, is within the first time limit and may indicate a potential nodal rhythm. If the A-V interval (AVint) is not within the second time limit (here, 60 ms) indicating that there is no nodal rhythm present, the method proceeds to block 170, which increments the sinus rhythm counter (ns).

Block 172 checks to see if the sinus rhythm counter is greater Nsd. If the sinus rhythm counter is not greater than Nsd, the method returns to the start at block 140. If the sinus rhythm counter is greater than the Nsd, sinus rhythm has been established and nodal treatment is no longer required, so nodal treatment is deactivated at block 174.

If the A-V interval (AVint) is within the second time limit (here, 60 ms) indicating that there may be nodal rhythm present, the method proceeds to block 176, which calculates a new escape interval. This point may also be reached from block 154 if an atrial pace was followed by a ventricular sense. The method calculates a new atrial escape interval (A_esc) which is tuned such that an hemodynamic AV delay is obtained, as the mean ventricular rate, less the paced AV interval, plus the V-A interval [A_esc=MVR−PAV+VAint]. The sinus rhythm counter (ns) is cleared at block 178.

Figure 8A:
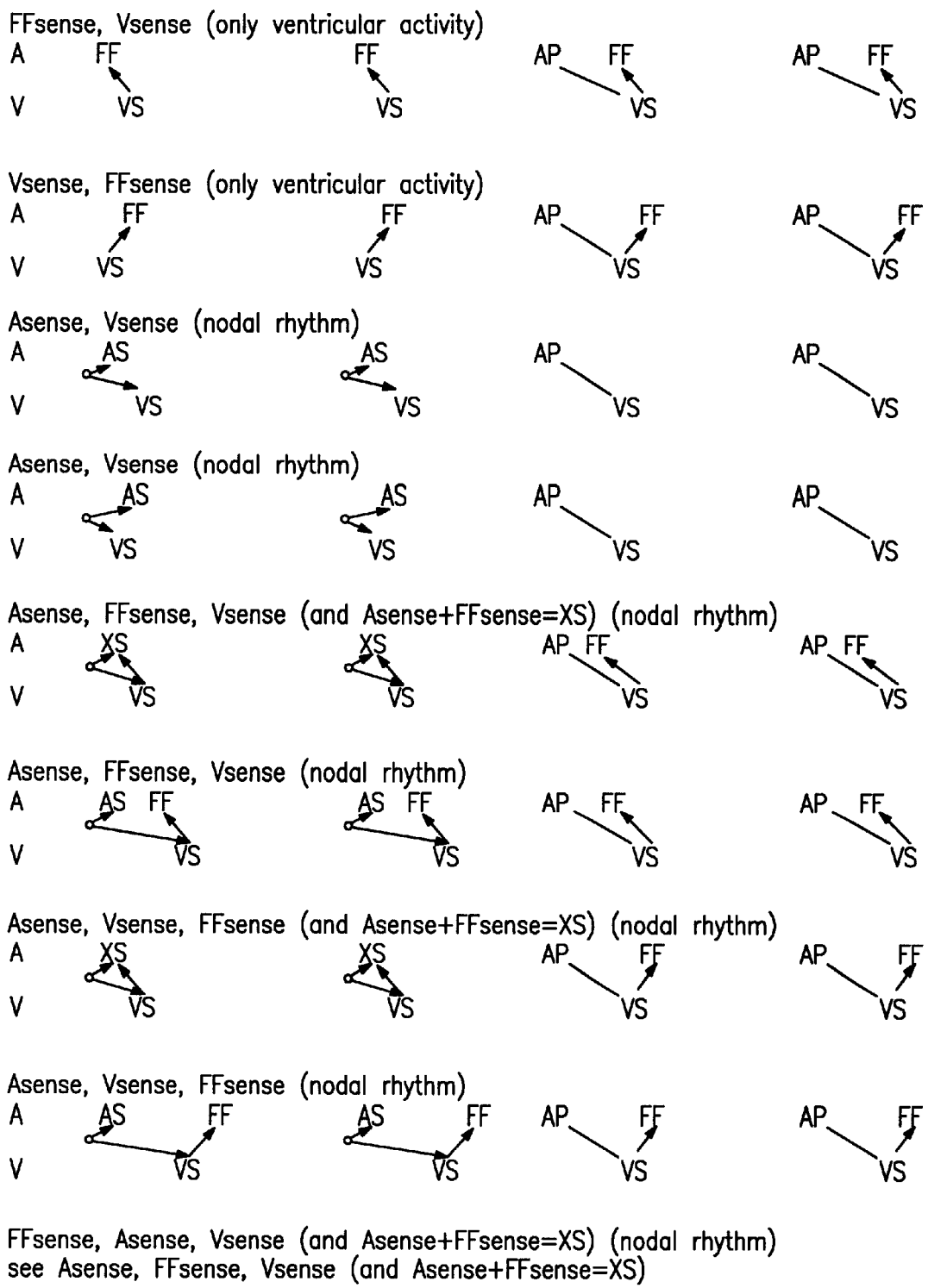
FIGS. 8A & 8B are cardiac activity schematic diagrams for nodal rhythm and atrial pacing response, in accordance with the present invention.
Figure 8B:
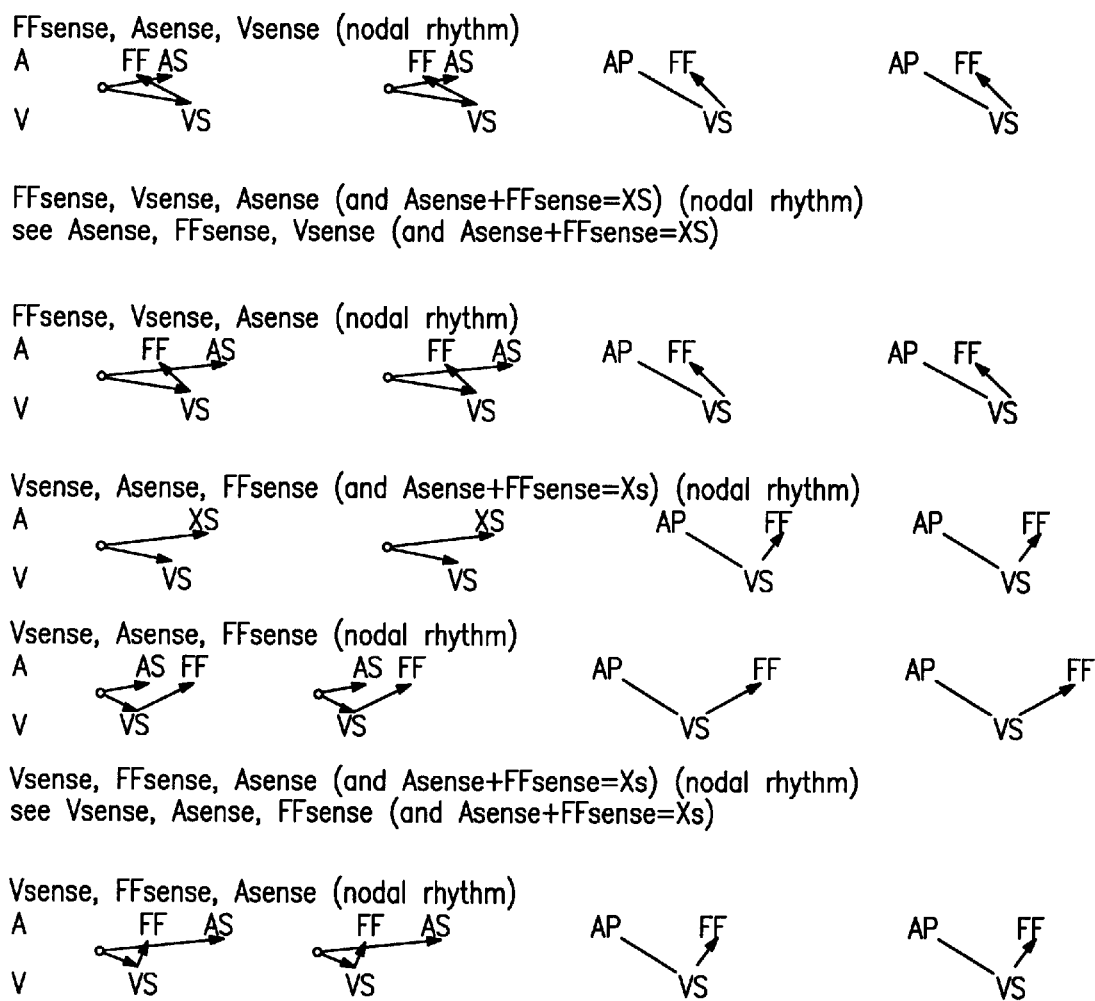

FIGS. 8A & 8B are cardiac activity schematic diagrams for nodal rhythm and atrial pacing response in accordance with the present invention. The diagrams show all possible sequences of atrial and ventricular sensing that might occur and demonstrate that the nodal rhythm detection and treatment method is effective even if a far field wave is present. The first two ventricular beats of each case are the cardiac activity before nodal treatment and the last two ventricular beats of each case are the cardiac activity with pacing on, as can be seen by the atrial paces (AP). The diagrams show the atrial, ventricular, far field, and combination sense. Far field sense is a ventricular contraction R wave sensed in the atrium. Far field senses have similar features as nodal atrial senses. They can be absent, but if present the illustrations show that the algorithm still works appropriately. Combination sense is an atrial sense and a far field sense occurring simultaneously (XS).

Using the "Asense, FFsense, Vsense (nodal rhythm)" case as an example, the (intrinsic) nodal activity is initiated at the AV node between the atrium and the ventricle. The atrial sense, then the far field sense, is detected in the atrium. The ventricular sense is then detected in the ventricle. The sequence repeats in the second diagram. In the third diagram, nodal treatment is active. An atrial pace is applied, then an atrial sense detected (this far field R wave is ignored in the AV delays), followed by a ventricular sense irrespective of far field R waves. The various cases illustrate that the nodal rhythm detection and treatment method will be effective for all possible sequences.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to a method of nodal rhythm detection and treatment. The present invention is also not limited to nodal rhythm detection and treatment algorithms per se, but may find further application as a means for detecting and treating nodal rhythm. The present invention further includes within its scope methods and systems for nodal rhythm detection and treatment as described above.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

We claim:

1. A method for nodal rhythm detection and delivery of therapy for a mammalian heart, comprising:

determining whether an atrial event precedes a ventricular event;

counting the consecutive times atrial events occur less than a first time limit before the ventricular event, if the atrial event precedes the ventricular event;

counting the consecutive times atrial events occur less than a second time limit after the ventricular event, if the atrial event follows the ventricular event; and delivering therapy for nodal rhythm if the number of times consecutive atrial events occur within a time period between the first time limit before a ventricular event and the second time limit after a ventricular event is greater than a nodal treatment activation constant.

2. The method of claim 1, wherein the nodal therapy delivery activation constant is 1 to 10.

3. The method of claim 2, wherein the nodal therapy delivery activation constant is 3.

4. The method of claim 1, wherein the first time limit and the second time limit are determined for a specific patient.

5. The method of claim 1, wherein the first time limit is 60 ms.

6. The method of claim 1, wherein the second time limit is 100 ms.

7. The method of claim 1, further comprising:

determining a mean ventricular rate;

determining a paced AV interval;

determining an AV interval if the atrial event precedes the ventricular event;

determining a VA interval if the atrial event follows the ventricular event;

calculating a new atrial escape interval by subtracting the paced AV interval from the sum of the AV interval and the mean ventricular rate, if the atrial event precedes the ventricular event; and calculating the new atrial escape interval by subtracting the paced AV interval and the VA interval from the mean ventricular rate, if the atrial event follows the ventricular event.

8. The method of claim 1, wherein said therapy delivery for nodal rhythm comprises delivery of treatment in response to an alarm.

9. The method of claim 1, wherein said therapy delivery for nodal rhythm comprises delivery of treatment by an implantable medical device.

10. An implantable medical system for delivering therapy to a mammalian heart, comprising:

means for determining whether an atrial even precedes a ventricular event;

means for counting the consecutive times atrial events occur less than a first time limit before the ventricular event, if the atrial event precedes the ventricular event;

means for counting the consecutive times atrial events occur less than a second time limit after the ventricular event, if the atrial event follows the ventricular event; and means for delivering the therapy for nodal rhythm if the number of times consecutive atrial events occur within a time period between the first time limit before a ventricular event and the second time limit after a ventricular event is greater than a nodal treatment activation constant.

11. The system of claim 10, wherein the nodal therapy delivery activation constant is 1 to 10.

12. The system of claim 11, wherein the nodal therapy delivery activation constant is 3.

13. The system of claim 10, wherein the first time limit and the second time limit are determined for a specific patient.

14. The system of claim 10, wherein the first time limit is 60 ms.

15. The system of claim 10, wherein the second time limit is 100 ms.

16. The system of claim 10, further comprising:

means for determining a mean ventricular rate;

means for determining a paced AV interval;

means for determining an AV interval if the atrial event precedes the ventricular event;

means for determining a VA interval if the atrial event follows the ventricular event;

means for calculating a new atrial escape interval by subtracting the paced AV interval from the sum of the AV interval and the mean ventricular rate, if the atrial event precedes the ventridular event; and means for calculating the new atrial escape interval by subtracting the paced AV interval and the VA interval from the mean ventricular rate, if the atrial event follows the ventricular event.

17. A computer usable medium storing computer readable program code having a program for nodal rhythm detection and treatment for a mammalian heart, comprising:

computer readable program code for determining whether an atrial event precedes a ventricular event;

computer readable program code for counting the consecutive times atrial events occur less than a first time limit before the ventricular event, if the atrial event precedes the ventricular event;

computer readable program code for counting the consecutive times atrial events occur less than a second time limit after the ventricular event, if the atrial event follows the ventricular event; and computer readable program code for delivering therapy for nodal rhythm if the number of times consecutive atrial events occur within a time period between the first time limit before a ventricular event and the second time limit after a ventricular event is greater than a nodal treatment activation constant.

18. The program of claim 17, wherein the nodal therapy delivery activation constant is 1 to 10.

19. The program of claim 18, wherein the nodal therapy delivery activation constant is 3.

20. The program of claim 17, wherein the first time limit and the second time limit are determined for a specific patient.

21. The program of claim 17, wherein the first time limit is 60 ms.

22. The program of claim 17, wherein the second time limit is 100 ms.

23. The program of claim 17, further comprising:

computer readable program code for determining a mean ventricular rate;

computer readable program code for determining a paced AV interval;

computer readable program code for determining an AV interval if the atrial event precedes the ventricular event;

computer readable program code for determining a VA interval If the atrial event follows the ventricular event;

computer readable program code for calculating a new atrial escape interval by subtracting the paced AV interval from the sum of the AV interval and the mean ventricular rate, if the atrial event precedes the ventricular event; and computer readable program code for calculating the new atrial escape interval by subtracting the paded AV interval and the VA interval from the mean ventricular rate, if the atrial event follows the ventricular event.

* * * * *